United States Patent [19]
Lai

[11] Patent Number: 5,639,908
[45] Date of Patent: Jun. 17, 1997

[54] UREA AND URETHANE MONOMERS FOR CONTACT LENS MATERIALS

[75] Inventor: Yu-Chin Lai, Pittsford, N.Y.

[73] Assignee: Bausch & Lomb Incorporated, Rochester, N.Y.

[21] Appl. No.: 442,216

[22] Filed: May 16, 1995

Related U.S. Application Data

[62] Division of Ser. No. 169,824, Dec. 17, 1993, Pat. No. 5,451,651.

[51] Int. Cl.$^6$ .................. C07C 269/00; C07C 275/14; C07C 275/16
[52] U.S. Cl. ................ 560/158; 560/115; 564/57; 564/60
[58] Field of Search .................. 560/158, 205, 560/115; 564/32, 47, 57, 58, 60

[56] References Cited

U.S. PATENT DOCUMENTS

| | | | |
|---|---|---|---|
| 2,544,638 | 3/1951 | Caldwell et al. | 260/77.5 |
| 3,671,492 | 6/1972 | Nakaguchi et al. | 260/85.5 |
| 3,931,311 | 1/1976 | Thomas et al. | 260/552 |
| 4,223,041 | 9/1980 | Pigerol et al. | 424/322 |
| 4,250,322 | 2/1981 | Efimov et al. | 560/26 |
| 4,584,143 | 4/1986 | Falk | 558/240 |
| 4,668,550 | 5/1987 | Tajima et al. | 428/65 |
| 4,705,885 | 11/1987 | Just et al. | 560/158 |
| 4,772,695 | 9/1988 | Olofson et al. | 540/467 |
| 5,006,622 | 4/1991 | Kunzler | 526/309 |
| 5,034,461 | 7/1991 | Lai | 525/100 |
| 5,070,165 | 12/1991 | Muller et al. | 526/301 |
| 5,070,215 | 12/1991 | Bambury et al. | 556/418 |
| 5,079,356 | 1/1992 | Huth | 540/524 |
| 5,144,056 | 9/1992 | Lina et al. | 560/25 |

FOREIGN PATENT DOCUMENTS 2 063 248   6/1981   United Kingdom ........ C07C 125/065

OTHER PUBLICATIONS

C. G. Overberger, G. Montaudo, and S. Ishida, Journal of Polymer Science: Part A–1, vol. 7, 35–46, (1969).
Chemical Abstracts, vol. 63, 10124, 1965.

*Primary Examiner*—Joseph L. Schofer
*Assistant Examiner*—Wu C. Cheng
*Attorney, Agent, or Firm*—John E. Thomas

[57] ABSTRACT

Urea- and urethane-containing monomers for contact lens materials are disclosed.

9 Claims, No Drawings

UREA AND URETHANE MONOMERS FOR CONTACT LENS MATERIALS

This is a divisional of application Ser. No. 08/169,824 filed on Dec. 17, 1993 U.S. Pat. No. 5,451,651.

BACKGROUND OF THE INVENTION

The present invention relates to novel urea and urethane monomers. The monomers are useful as strengthening agents for contact lens copolymeric materials, especially hydrogel contact lens materials.

Various monomeric components are known to increase modulus and tear strength when incorporated in copolymeric systems, such as hydrogels used for contact lenses. As an example, compounds such as 2-hydroxy-4-t-butylcyclohexyl methacrylate (TBE) have been disclosed as a strengthening agent in various hydrogel formulations (U.S. Pat. No. 5,006,622). A characteristic feature of such strengthening agents is that they are bulky and are sometimes difficult to synthesize.

SUMMARY OF THE INVENTION

In a first aspect, the invention relates to monomers selected from compounds of the general formula (I):

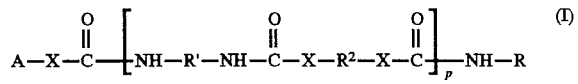

wherein:
A is an ethylenically unsaturated polymerizable radical;
each X is independently —O— or —NH—;
R is a monovalent radical having 5 to 30 carbon atoms selected from the group consisting of branched alkyl, optionally substituted cycloalkyl, optionally substituted alkylcycloalkyl, optionally substituted aryl, and optionally substituted alkylaryl;
each R' is independently a divalent radical having 5 to 30 carbon atoms selected from the group consisting of branched alkylene, optionally substituted cycloalkylene, optionally substituted alkylene-cycloalkylene, optionally substituted arylene, and optionally substituted alkylene-arylene;
each $R^2$ is independently a divalent organic radical; and
p is 0, 1 or 2.

In another aspect, the invention relates to shaped articles which are formed of the polymerization product of a mixture comprising a monomer of formula (I) and a hydrophilic monomer. According to preferred embodiments, the article is optically clear and shaped as a contact lens.

According to further aspects, the invention relates to monomers selected from compounds of the general formula (II), and shaped articles, such as contact lenses, which are formed of the polymerization product of a mixture comprising the monomer and a hydrophilic monomer:

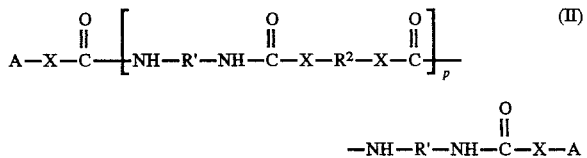

wherein:
each A is independently an ethylenically unsaturated polymerizable radical;
each X is independently —O— or —NH—;
R' and $R^2$ are as defined for formula (I); and
p is 0, 1 or 2.

The monomers of this invention function especially well as a comonomer for hydrogel copolymeric materials, and the monomers can be synthesized relatively easily. The monomers can be used to tailor desired properties of the copolymer, including an increase in tensile strength, modulus and/or tear strength of the resultant copolymer.

DETAILED DESCRIPTION OF PREFERRED EMBODIMENTS

In a first aspect, the invention relates to monomers selected from compounds of formula (i) described above. Preferred monomers include urethane derivatives, wherein X in formula is —O—, and urea derivatives wherein X is —NH—.

In formula (I) R represents a relatively "bulky" radical. It is desired that the monomers act as strengthening agents for copolymers, providing increased tensile strength, modulus and/or tear strength. Since the monomers include at least one "bulky" radical, the monomers can be used to impart rigidity and strength to the copolymeric material prepared therefrom.

Representative radicals for R include monovalent radicals having 5 to 30 carbon atoms, including: branched alkyl, such as neopentyl; optionally substituted cycloalkyl, such as cyclopentyl, cyclohexyl, or derivatives thereof wherein the cyclohexyl ring is substituted with one or more $C_1$–$C_6$ alkyl radicals; optionally substituted alkylcycloalkyl, such as ethylcyclohexyl; optionally substituted aryl, such as phenyl or derivatives thereof wherein the phenyl ring is substituted with one or more $C_1$–$C_6$ alkyl radicals; and optionally substituted alkylaryl, such as benzyl or derivatives thereof wherein the phenyl ring is substituted with one or more $C_1$–$C_6$ alkyl radicals.

R' represents a relatively "bulky" divalent radical. Representative radicals for R' include divalent radicals having 5 to 30 carbon atoms, including: branched alkylene, such as neopentylene; optionally substituted cycloalkylene, such as 1,3-cyclopentylene, 1',4'-cyclohexylene, or derivatives thereof wherein the cyclohexyl ring is substituted with one or more $C_1$–$C_6$ alkyl radicals; optionally substituted alkylene-cycloalkylene, such as ethylenecyclohexylene, 1,4-dimethylene-cyclohexylene or methylene-1,5,5-trimethyl-1,3-cyclohexylene; optionally substituted arylene, such as 1,4-phenylene, 1',3-phenylene, 4,4'-diphenylene, or derivatives thereof wherein the phenyl ring is substituted with one or more $C_1$–$C_6$ alkyl radicals; and optionally substituted alkylene-arylene, such as 1,4-dimethylenephenylene.

$R^2$ in formula (I) is a divalent organic radical. This radical is the residue of an α,ω-dihydroxyl reactant or an α,ω-diamino reactant (wherein the terminal hydroxyl or amino radicals react with an isocyanate reactant to form the urethane or urea linkage, respectively). Representative diamino compounds include 1,2-ethylenediamine, 1,4-phenylenediamine, 1,6-hexamethylenediamine and 1,4-cyclohexyldiamine. Representative dihydroxyl compounds include neopentyl glycol, 1,2-ethanediol, 1,6-hexanediol, triethyleneglycol, bisphenol A, 1,4-cyclohexanedimethanol, 1,2-propanediol, and 2,2,3,3,4,4-hexafluoropentane-1,5-diol. Accordingly, preferred $R^2$ radicals include $C_1$–$C_{10}$ alkylene, $C_1$–$C_{10}$ haloalkylene such as $C_1$–$C_{10}$ fluoroalkylene, $C_2$–$C_{10}$ alkylene ethers, $C_6$–$C_{10}$ arylene, $C_6$–$C_{10}$ haloarylene, $C_7$–$C_{10}$ alkylarylene, $C_7$–$C_{10}$ haloalkylarylene, and $C_5$–$C_{10}$ cycloalkylene. Optionally, the $R^2$ radical may correspond to the "bulky" radicals described above for R'.

Representative polymerizable radicals for A include those of the formula (III):

$$R^3-CH=C(R^6)-(CH_2)_w-(R^5)_x-(Ar)_y-(CH_2)_z- \quad \text{(III)}$$

wherein:

$R^3$ is selected from the group consisting of hydrogen, an alkyl radical having 1 to 6 carbon atoms, and an $R^4$—Y—CO— radical wherein $R^4$ is an alkyl radical having 1 to 12 carbon atoms and Y is —O—, —S— or —NH—;

$R^5$ is selected from the group consisting of —COO—, —OCO—, —CONH—, —NHCO—, —OCOO—, —NHCOO— and —OCO—NH—;

$R^6$ is selected from the group consisting of hydrogen and methyl;

Ar is an aromatic radical having 6 to 12 carbon atoms;

w is 0 or an integer of 1 to 6;

x is 0 or 1;

y is 0 or 1; and z is 0 or an integer of 1 to 10.

A preferred class of polymerizable radicals are represented by the formula:

$$CH_2=C(R^6)-COO-(CH_2)_z- \quad \text{(IV)}$$

where z is as previously defined.

The monomers of formula (I) are especially useful for increasing tear strength of hydrogel copolymeric contact lens materials.

A second preferred class of monomers include the difunctional monomers of formula (II), described above, containing two ethylenically unsaturated polymerizable radicals. Preferred monomers include urethane derivatives wherein each X in formula (II) is —O—, and urea derivatives wherein each X is —NH—.

The A radicals in formula (II), which may the same or different, are preferably a radical chosen from those represented by formula (III), more preferably, a radical chosen from those represented by formula (IV).

In formula (II), R' represents a relatively "bulky" divalent radical. Representative radicals for R' include those discussed above. $R^2$ in formula (II) is a divalent organic radical, as discussed for formula (I) compounds.

This latter class of monomers are especially useful for increasing modulus of the copolymer, since, in addition to increasing rigidity of the copolymer, the difunctional monomers provide crosslinking.

The monomers of the invention may be synthesized according to general methods known in the art from precursors that are commercially available or that can be synthesized by methods known to those skilled in the art. Generally, urethane-containing monomers can be synthesized by reacting desired isocyanate precursors with hydroxyl-terminated precursors, and urea-containing monomers can be synthesized by reacting desired isocyanate precursors with amino-terminated precursors.

The monofunctional urethane-containing or urea-containing monomers of formula (I) may be prepared according to the following general reaction schemes. For purposes of illustration, the monomers correspond to formula (I) where p is 0.

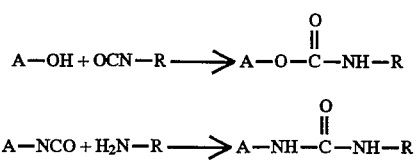

A detailed synthesis involving the above schemes is described in Examples 1 and 2, infra.

The difunctional monomers of formula (II) can be prepared by, first, reacting diisocyanate precursors (generally containing the "bulky" R' divalent radical) with the aforementioned α,ω-dihydroxyl reactants or α,ω-diamino reactants (generally containing the $R^2$ divalent radical), at a desired ratio, followed by endcapping the resultant product with ethylenically unsaturated polymerizable radicals. A representative scheme is described in Example 3, infra.

In another aspect, the invention relates to shaped articles which are formed of the polymerization product of a mixture comprising a monomer of this invention and a hydrophilic monomer.

Preferably, the monomeric mixture from which the article is formed includes at least one monomer of formula (I) or (II) in an amount of about 5 to 95 weight percent (more preferably from about 5 to 50 weight percent, with about 5 to about 30 percent being especially preferred), and at least one hydrophilic monomer in an amount of from about 5 to 95 weight percent (more preferably from about 50 to about 95 weight percent), based on total weight of the monomeric components. According to preferred embodiments, the article is optically clear and shaped as a contact lens, including rigid, gas permeable copolymeric materials and hydrogel copolymeric materials. Hydrogel copolymers are especially preferred.

A hydrogel is a hydrated cross-linked polymeric system that contains water in an equilibrium state prepared by polymerizing a monomeric mixture containing at least one hydrophilic monomer. The hydrophilic monomer or the formula (II) monomer may function as a crosslinking agent (a crosslinker being defined as a monomer having multiple polymerizable functionalities), or a separate crosslinking monomer may be included in the monomeric mixture. In the case of silicone hydrogels, a silicone-containing monomer is included in the monomeric mixture.

Suitable hydrophilic monomers include: ethylenically unsaturated carboxylic acids, such as methacrylic acid and acrylic acid; (meth)acrylic substituted alcohols, such as 2-hydroxyethyl methacrylate and 2-hydroxyethyl acrylate; vinyl lactams, such as N-vinyl pyrrolidone; and acrylamides, such as (meth)acrylamide and N,N-dimethyl (meth)acrylamide. (As used herein, the term "(meth)" designates optional methyl substitution. Thus, terms such as "(meth)acrylate" denote acrylate radicals and methacrylate radicals.) Other suitable hydrophilic monomers will be apparent to one skilled in the art.

Representative crosslinking monomers include: divinyl monomers such as divinylbenzene; allyl methacrylate; di(meth)acrylate monomers such as ethyleneglycol di(meth)acrylate, tetraethyleneglycol di(meth)acrylate, and polyethyleneglycol di(meth)acrylate; and vinylcarbonate derivatives of the glycol di(meth)acrylates, i.e., compounds wherein at least one (meth)acrylate radical is replaced with a vinylcarbonate group, such as methacryloxyethyl vinylcarbonate having the formula:

This latter crosslinking monomer is preferred when the hydrophilic monomer contains vinyl functionality other than a (meth)acrylate group, such as N-vinyl-2-pyrrolidone. Preferably, the crosslinking monomer is included in the monomeric mixture at about 0.01 to about 10 weight percent based on total weight of the monomeric components.

The monomeric mixtures including the monomers of the present invention, when copolymerized, are readily cured to cast shaped articles by methods such as UV polymerization, thermal polymerization, or combinations thereof. Representative thermal polymerization initiators are organic peroxides, such as for example acetal peroxide, lauroyl peroxide, decanoyl peroxide, stearoyl peroxide, benzoyl peroxide, tertiary butyl peroxypivalate and peroxydicarbonate in a concentration of about 0.01 to 2 percent by weight of the total monomer mixture. Representative UV initiators are those known in the field such as, benzoin methyl ether, benzoin ethyl ether, Darocur-1173, 1164, 2273, 1116, 2959, 3331 (EM Industries) and Igracure 651 and 184 (Ciba-Geigy). The monomeric mixture may also include other monomers or components as will be apparent to one skilled in the art, for example, colorants or UV-absorbing agents.

In producing contact lenses, the monomeric mixture may be cured in tubes to provide rod-shaped articles, which are then cut into buttons. The buttons may then be lathed into contact lenses. Alternately, contact lenses may be cast directly in molds from the monomeric mixtures, such as by spincasting and static casting methods. As an additional method, an excess of a monomeric mixture can be cured by spincasting in a mold to form a shaped article having an anterior lens surface and a relatively large thickness, and the posterior surface of the cured spincast article is subsequently lathed to provide a contact lens having the desired thickness and posterior lens surface.

The following examples further illustrate various preferred embodiments.

EXAMPLE 1

Synthesis of 1-cyclohexyl-3-methacryloxyethyl carbamate

A 3-neck 250-mL round bottom flask equipped with a reflux condenser was charged with 2-hydroxyethyl methacrylate (6.7185 g), 1,1'-bi-2-naphthol (1.3 mg), cyclohexyl isocyanate (6.100 g), dibutyltin dilaurate (49 mg) and 50 mL of methylene chloride. The mixture was then stirred until the IR spectrum of the product indicated no NCO peak (16 hours). The solution was filtered and evaporated to dryness to recover the product. The product was characterized by H-NMR, 0.70–2.10 ppm. (m, 10H), 1.92 ppm (s, 3H), 3.42 ppm (m, 1H), 4.22 ppm (s, 4H), 4.92 ppm (b, 1H), 5.50 ppm (s, 1H), 6.10 ppm (s, 1H).

EXAMPLE 2

Synthesis of 1-cyclohexyl-3-methacryloxyethyl urea

A 3-neck, 250-mL round bottom flask equipped with a reflux condenser was charged with isocyanatoethyl methacrylate (7.79 g), 1,1'-bi-2-naphthol (1.3 mg) and 50 mL of methylene chloride. While stirring, cyclohexylamine (5.24 g) and dibutyltin dilaurate (52.3 mg) in 50 mL of methylene chloride were added over a 15 minute period. The reaction mixture was kept stirred for an additional 30 minutes. The solution was filtered and evaporated to dryness to recover the product. The product was characterized by H-NMR, 0.72–2.10 ppm (m, 1H), 1.90 ppm (s, 3H), 3.45 ppm (t, 2H), 3.50 ppm (hidden, 1H), 4.18 ppm (t, 2H), 5.12 ppm (s, 1H), 5.26 ppm (s, 1H), 5.52 ppm (s, 1H), 6.10 ppm (s, 1H).

EXAMPLE 3

Synthesis of a Urethane Dimethacrylate

To a 3-neck round bottom flask equipped with a reflux condenser were added isophorone diisocyanate (6.6639 g, 0.03 mol), diethyleneglycol (2.1260 g, 0.02 mol), dibutyltin dilaurate (96.1 mg) and 60 mL of methylene chloride. The contents were refluxed for 6 hours, then cooled to room temperature. To the contents were added 2-hydroxyethyl methacrylate (3.091 g) and 1,1'-bi-2-naphthol (1.2 mg). The mixture was then stirred until the NCO peak disappeared (48 hours). The solution was filtered and evaporated to dryness to recover the product, a mixture of dimethacrylate urethane isomers. One isomer is the dimethacrylate urethane shown below, wherein each R' is the hydrocarbyl residue of the isophorone diisocyanate and each A is 2-ethylmethacrylate:

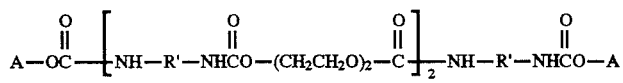

EXAMPLES 4–9

The mixtures listed in Table 1 were cast between two glass plates and cured under UV light for 2 hours. The resultant films were released and boiled in deionized water for 4 hours and then placed in buffered saline. The water content and mechanical properties were then measured. The amounts listed in Table 1 are parts by weight. It is noted that the Control (C1) included no monomer of the present invention.

TABLE 1

| | Example No. | | | | | | |
|---|---|---|---|---|---|---|---|
| Component | C1 | 4 | 5 | 6 | 7 | 8 | 9 |
| HEMA | 55 | 55 | 55 | 55 | 55 | 55 | 55 |
| NVP | 45 | 45 | 45 | 45 | 45 | 45 | 45 |
| HEMAVC | 0.2 | 0.2 | 0.2 | 0.2 | 0.2 | 0.2 | 0.2 |
| DAROCUR-1173 | 0.2 | 0.2 | 0.2 | 0.2 | 0.2 | 0.2 | 0.2 |
| Glycerin | 20 | 20 | 20 | 20 | 20 | 20 | 20 |
| Urethane MA* | — | — | — | — | 5 | 10 | 15 |
| Urea MA** | — | 5 | 10 | 15 | — | — | — |
| % Water | 71.2 | 63.5 | 60.3 | 55.1 | 69.4 | 67.6 | 61.4 |
| Tear | 0.5 | 1.4 | 2.2 | 3.3 | 1.1 | 2.3 | 3.6 |
| Modulus | 9 | 10 | 15 | 12 | 10 | 8 | 10 |

*Compound of Example 1
**Compound of Example 2

EXAMPLE 10

The following mixtures were cast into copolymeric hydrogel films following the procedure of Example 4. It is noted that formulation C2 included no monomer of the present invention.

TABLE 2

| Example | C2 | 10 |
|---|---|---|
| Formulation: | | |
| HEMA | 31.8 | 31.8 |
| NVP | 44.7 | 44.7 |
| HEMAVC | 0.5 | 0.5 |
| DAROCUR-1173 | 0.2 | 0.2 |
| Glycerin | 15 | 15 |
| Tint | 0.006 | 0.006 |
| TBE | 7.95 | — |
| Urethane DiMA* | — | 7.95 |
| Tensile | 9 | 22 |
| Tear | 1.2 | 2.0 |
| Modulus | 10 | 75 |
| % Elongation | 110 | 35 |

*Urethane dimethacrylate monomer described in Example 3

EXAMPLES 11–12

The mixtures listed in Table 3 were cast into copolymeric hydrogel films following the procedure of Example 4. Formulations C3 and C4 included no monomer of the present invention.

TABLE 3

| Component | C3 | 11 | 12 | C4 |
|---|---|---|---|---|
| HEMA | 55 | 55 | 55 | 55 |
| NVP | 45 | 45 | 45 | 45 |
| HEMAVC | 0.5 | 0.5 | 0.5 | 0.5 |
| DAROCUR-1173 | 0.2 | 0.2 | 0.2 | 0.2 |
| Glycerin | 20 | 20 | 20 | 20 |
| Urethane MA* | — | 15 | — | — |
| Urea MA** | — | — | 15 | — |
| TBE | — | — | — | 15 |
| % Water | 69 | 56 | 54 | 53 |
| Tear | 3.6 | 7.4 | 5.5 | 13 |
| Modulus | 30 | 45 | 55 | 30 |

*Compound of Example 1
**Compound of Example 2

Many other modifications and variations of the present invention are possible to the skilled practitioner in the field in light of the teachings herein. It is therefore understood that, within the scope of the claims, the present invention can be practiced other than as herein specifically described.

I claim:

1. A monomer selected from compounds of the general formula:

$$A-X-\overset{O}{\underset{\|}{C}}-\left(NH-R'-NH-\overset{O}{\underset{\|}{C}}-X-R^2-X-\overset{O}{\underset{\|}{C}}\right)_p \quad (II)$$

-continued $$-NH-R'-NH-\overset{O}{\underset{\|}{C}}-X-A$$

wherein:
each A is independently an ethylenically unsaturated polymerizable radical;
each X is independently —O— or —NH—;
each R' is independently a divalent radical having 5 to 30 carbon atoms selected from the group consisting of optionally substituted cycloalkylene and optionally substituted alkylene-cycloalkylene;
each $R^2$ is independently a divalent organic radical; and
p is 1 or 2.

2. A monomer of claim 1, wherein each X is —NH—.

3. A monomer of claim 1, wherein each X is —O—.

4. A monomer of claim 3, wherein each $R^2$ is a divalent alkylene ether radical.

5. A monomer of claim 4, wherein each R' is $C_6$–$C_{12}$ alkylene-cycloalkylene substituted with $C_1$–$C_6$ alkyl.

6. A monomer of claim 1, wherein each A is a radical of the formula:

$$R^3-CH=\overset{\overset{R^6}{|}}{C}-(CH_2)_w-(R^5)_x-(Ar)_y-(CH_2)_z-$$

wherein:
$R^3$ is selected from the group consisting of hydrogen, an alkyl radical having 1 to 6 carbon atoms, and an $R^4$—Y—CO— radical wherein $R^4$ is an alkyl radical having 1 to 12 carbon atoms and Y is —O—, —S—, or —NH—;
$R^5$ is selected from the group consisting of —COO—, —OCO—, —CONH—, —NHCO—, —OCOO—, —NHCOO— and OCO—NH—;
$R^6$ is selected from the group consisting of hydrogen and methyl;
Ar is an aromatic radical having 6 to 12 carbon atoms;
w is 0 or an integer of 1 to 6;
x is 0 or 1;
y is 0 or 1; and
z is 0 or an integer of 1 to 10.

7. A monomer of claim 6, wherein each A is a radical of the formula:

$$CH_2=\overset{\overset{R^6}{|}}{C}-COO-(CH_2)_z-$$

8. A monomer of claim 5, wherein each A is 2-ethylmethacrylate and each R' is the hydrocarbyl residue of isophorone diisocyanate.

9. A monomer of claim 8, wherein p is 2 and each $R^2$ is —(CH$_2$CH$_2$OCH$_2$CH$_2$)—.

* * * * *